United States Patent
González (10) Patent No.: US 9,861,780 B2
(45) Date of Patent: Jan. 9, 2018

(54) BLADDER CATHETER (71) Applicant: RETHINK MEDICAL SL., Las Palmas de Gran Canaria (ES)

(72) Inventor: Manuel Luque González, Malaga (ES)

(73) Assignee: RETHINK MEDICAL SL., Las Palmas de Gran Canaria (ES)

( * ) Notice: Subject to any disclaimer, the term of this patent is extended or adjusted under 35 U.S.C. 154(b) by 431 days.

(21) Appl. No.: 14/414,216

(22) PCT Filed: Jul. 10, 2013

(86) PCT No.: PCT/EP2013/064520
§ 371 (c)(1),
(2) Date: Jan. 12, 2015

(87) PCT Pub. No.: WO2014/009389
PCT Pub. Date: Jan. 16, 2014

(65) Prior Publication Data
US 2015/0202407 A1  Jul. 23, 2015

(30) Foreign Application Priority Data

Jul. 13, 2012  (DE) .................. 20 2012 006 814

(51) Int. Cl.
*A61M 39/22* (2006.01)
*A61M 25/00* (2006.01)

(52) U.S. Cl.
CPC ...... *A61M 25/0017* (2013.01); *A61M 39/223* (2013.01); *A61M 2025/0018* (2013.01);
(Continued)

(58) Field of Classification Search
CPC .... A61M 2025/0018; A61M 2039/224; A61M 2205/7536; A61M 25/0017; A61M 39/223
See application file for complete search history.

(56) References Cited

U.S. PATENT DOCUMENTS 4,306,705 A    12/1981  Svensson
4,917,271 A *   4/1990  Kanner ............... B05B 11/0021
                                                  222/189.08
(Continued)

FOREIGN PATENT DOCUMENTS

AT         4 556 E       9/1983
DE    202008017850 U1   10/2010
(Continued)

OTHER PUBLICATIONS

Mar. 27, 2013 German Examination Report for German Patent Application No. 10 2012 006 814.8.
Oct. 11, 2013 International Search Report for PCT/EP2013/064520.

*Primary Examiner* — Tatyana Zalukaeva
*Assistant Examiner* — Kai Weng
(74) *Attorney, Agent, or Firm* — Howard & Howard Attorneys PLLC (57) ABSTRACT

A bladder catheter includes a tube, wherein the tube has an insertion section for inserting into a urinary bladder through a urethra and wherein the tube has a connection section for connecting connection elements, wherein fluid can be drained from the urethra at the connection section via the insertion section, wherein a closable valve is arranged between the insertion section and the connection section in such a way that the discharge of fluid from the connection section can be prevented while the valve is closed.

6 Claims, 6 Drawing Sheets

(52) U.S. Cl.
CPC ............... *A61M 2039/224* (2013.01); *A61M 2205/7536* (2013.01)

(56) References Cited

U.S. PATENT DOCUMENTS

| | | |
|---|---|---|
| 5,429,620 A | 7/1995 | Davis |
| 5,460,606 A | 10/1995 | Daneshvar |
| 5,476,434 A | 12/1995 | Kalb et al. |
| 6,902,146 B1 | 6/2005 | Elliott |
| 2005/0148999 A1 | 7/2005 | Beaufore et al. |
| 2006/0095019 A1 | 5/2006 | Dikeman et al. |
| 2006/0212024 A1 | 9/2006 | Blake |

FOREIGN PATENT DOCUMENTS

| | | |
|---|---|---|
| EP | 0028601 B1 | 8/1983 |
| WO | 8001507 A1 | 7/1980 |
| WO | 2008144622 A1 | 11/2008 |

\* cited by examiner

BLADDER CATHETER

CROSS-REFERENCE TO RELATED APPLICATION

This application is based upon and claims priority as the National Stage Entry of PCT Patent Application No. EP2013/064520, filed on Jul. 10, 2013.

BACKGROUND OF THE INVENTION

1. Field of the Invention

The present invention relates, generally, to catheters and, more specifically, to a bladder catheter.

2. Description of the Related Art

The invention relates to a urinary catheter with a tube, wherein the tube has an insertion section for insertion in a bladder via a urethra, and wherein the tube has a connecting section for the connection of connection elements thereto, wherein liquid from the urethra can be discharged at the connecting section via the insertion section, wherein a closeable valve is disposed between the insertion section and the connecting section, such that a discharge of liquid from the connecting section when the valve is closed can be prevented.

A number of urinary catheters of this type are known from the prior art, and can no longer be dispensed with in the medical field. Urinary catheters of this type are used, for example in hospitals, with patients who can no longer leave their bed due to an operation or due to their age. These types of urinary catheters are also used with other disruptions pertaining to the voiding of the bladder. Different forms of these transurethral urinary catheters, meaning urinary catheters that are inserted into the bladder via the urethra, are known. Thus, there are, for example, intermittent catheters, which are removed from the urethra after a single voiding of the bladder. With indwelling catheters, which are normally designed as at least a two-way catheter, a balloon is disposed on the tip of the urinary catheter, wherein the urinary catheter exhibits one channel for urine discharge, and one channel for filling the balloon when the urinary catheter is inserted. The urinary catheter is then anchored long-term in the urethra.

Moreover, three-way catheters, the so-called flushing catheter, are also known from the prior art. In contrast to a two-way catheter, these urinary catheters exhibit an additional channel, through which flushing solutions can be introduced into the bladder. These three-way catheters are used, for example, if there is heavy bleeding in the bladder, in order to prevent blood clotting in the bladder by flushing the bladder. Other urinary catheters are known, for example, from DE 20 2008 017 850 U1, U.S. Pat. No. 5,429,620 A, U.S. Pat. No. 5,476,534 A, US 2006/095019A1, US 2006/212024 A1, U.S. Pat. No. 6,902,146 B1, WO2008/144622 and US 2005/148999 A1.

These urinary catheters known from the prior art exhibit certain disadvantages however. The known urinary catheters must be equipped with a urine bag for collecting the urine discharged from the connecting section. When a urine bag of this type is replaced, meaning when the urine bag is full, the connecting section must be held in place above the height of the urethra, because otherwise, urine can leak from the connecting section. Particularly in a hospital environment, this represents an unacceptable risk to the patient and the hospital staff. Furthermore, when the urine bag is connected, urine can be discharged into the urine bag at the connecting section through the insertion section at any time. Patients wearing a urinary catheter over a longer period of time thus lose their natural bladder reflex. After removing the urinary catheter, this can lead to problems pertaining to a natural "passing water" by the patient.

SUMMARY OF THE INVENTION

The present invention overcomes the disadvantages in the related art in providing a urinary catheter with which the comfort of a patient can be increased.

In this way, a urinary catheter having a valve, designed as a slide valve, has three switching settings, wherein the valve is closed in a closed setting and wherein the valve is air-permeable in a middle setting and wherein the valve is open in a releasing setting. This is advantageous because, then when the valve is closed, a full urine bag can be replaced, without urine being able to escape from the connecting section of the urinary catheter. It is thus not only more hygienic, but a urinary catheter of this type is also advantageous from an ecological perspective, because costs pertaining to hygienic measures in hospitals, for example, which until now have been necessary, can be eliminated by a urinary catheter of this type. With a slide valve, a particularly secure sealing can be enabled, while at the same time a very simple operation thereof is enabled. A patient or medical staff can then easily and securely discharge urine from a bladder, or further prevent the discharge of urine by closing the slide valve. The provision of three switching settings is particularly advantageous because the removal of air from the bladder of a patient is enabled in the middle setting, wherein a discharge of urine can be prevented.

The use of urine bags can also be avoided with a urinary catheter of this type. It can then be ensured, with a urinary catheter of this type, that a patient does not lose his bladder reflex. Instead, this remains intact. The use of a urine bag is no longer necessary because a patient can visit a toilet when he detects the feeling of a full bladder, wherein the patient can then void his bladder in a toilet by opening the closable valve. Particularly from an ergonomic perspective, a urinary catheter of this type can increase the comfort level of a patient to an enormous extent. A patient need not walk around with a urine bag. Instead, he is able to use conventional, public, for example, toilets. The urinary catheter can be hidden in the underwear after the bladder has been voided, without wetting the clothing.

In the night, a urine bag can then be connected to the connecting section of the urinary catheter, for collecting urine.

Advantageously, a urinary catheter of this type, or the tube, respectively, can be manufactured from rubber and/or latex and/or polyvinyl chloride (PVC) and/or silicone. Advantageously, the outer surface of the tube exhibits a hydrophilic coating, for increasing the sliding capacity into the urethra.

Furthermore, it is advantageous if an air-permeable filter and/or membrane section is provided in the valve. A filter and/or membrane section of this type can be disposed thereby, such that it enables air to escape when the valve is moved to the middle setting, wherein a discharge of urine can be prevented. It is advantageous that the filter and/or membrane section be manufactured from a hydrophobic acrylate polymer.

Further advantageously, the urinary catheter has a closed hollow tip with at least two opposing openings, in accordance with the Nelaton catheter design, at its end facing away from the connecting section. It is, however, also conceivable, that the urinary catheter is a Foley catheter. A Foley catheter exhibits a Nelaton tip, and has an additional balloon on its tip for securing the urinary catheter in the bladder. The design for this urinary catheter, as a Nelaton catheter, is advantageous, because the Nelaton catheter can be inserted particularly easily in a urethra of a patient.

It is also advantageous if the urinary catheter is a transurethral catheter. A transurethral urinary catheter can, in contrast to a suprapubic urinary catheter, be inserted in the bladder through the urethra of a patient.

Another advantageous design of the urinary catheter provides that the urinary catheter is an indwelling catheter. In this case, the urinary catheter can, in particular, be a two-way catheter, wherein urine can be discharged from the urethra through a central channel, while, on the other hand, a balloon, which can be provided on a tip of the urinary catheter, can be filled with water through a second channel. An indwelling catheter of this type can be disposed self-retaining in a urethra.

Another advantageous design of the urinary catheter provides that the urinary catheter is a flushing catheter. A flushing catheter of this type can, in particular, be a three-way catheter, with which, in contrast to a two-way catheter, a flushing solution can be introduced into a bladder through an additional third channel. In order to prevent blood clotting in the bladder, a bladder can be flushed with flushing liquids using a flushing catheter.

BRIEF DESCRIPTION OF THE DRAWINGS

Other objects, features, and advantages of the present invention will be readily appreciated as the same becomes better understood after reading the subsequent description taken in connection with the accompanying drawing wherein.

DETAILED DESCRIPTION OF THE INVENTION

Figure 1:
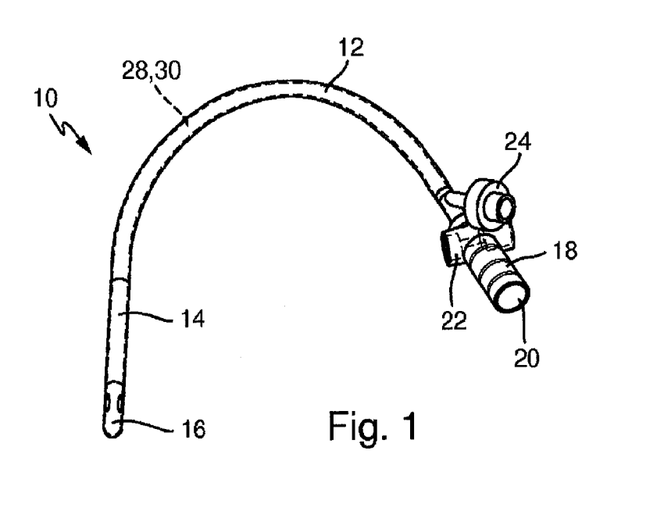
FIG. 1 shows a urinary catheter.

With reference now to the drawing(s), FIG. 1 shows a urinary catheter 10 with a tube 12. This tube 12 has an insertion section 14 with a tip 16, illustrated in greater detail in FIG. 2. This insertion section 12 can be at least partially inserted in a bladder of a patient through a urethra. The tube 12 has a connecting section 18 on its end facing away from the insertion section 14 or the tip 16, respectively. Connection elements can be inserted into this connecting section 18, or more specifically, into the opening 20 of the connecting section 18. The urinary catheter 10 has a valve 22 designed as a slide valve on its end facing the connecting section 18.

This valve 22 is disposed between the insertion section 14 and the connecting section 18, such that a discharge of urine from the opening 20, or the connecting section 18, respectively, can be prevented when the valve 22 is in a closed setting.

The urinary catheter 10 can be a so-called two-way catheter. The urinary catheter 10 thus has a connecting section 24 at its end facing the connecting section 18. A balloon can be disposed at the tip 16, and can be inflated with a liquid through this connecting section 24. Using this balloon, the urinary catheter 10 can be fixed in the bladder after it has been inserted in a bladder through a urethra. The urinary catheter 10 is thus retained in its position by the balloon. In order to fill the balloon, a secondary channel 30 is provided in the tube 12, separated from a main channel 28. If liquid can then enter the balloon at the connecting section 24 through the secondary channel 30, the balloon inflates and holds the urinary catheter 10 in position. The main channel 28, in turn, serves as a connection for the tip 16 of the urinary catheter 10 to the connecting section 18.

Figure 2:
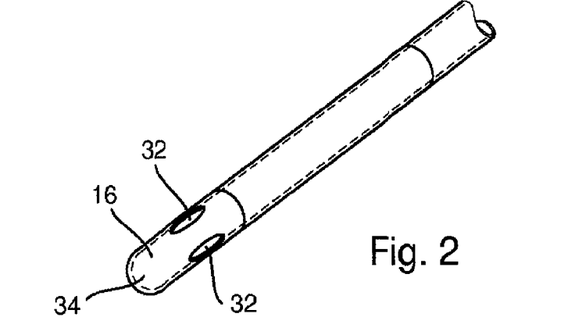
FIG. 2 shows an enlarged depiction of the tip of the urinary catheter.

Urine can be discharged at the tip 16 depicted in FIG. 2, when a urinary catheter 10 is inserted in a bladder, through two opposing eye-like openings 32, through the main channel 28 running in the insertion section 14, into a connection element connected at the connecting section 18, or directly into a toilet, respectively.

The tip 16 depicted in FIG. 2 represents a tip 16 of a urinary catheter configured as a so-called Nelaton catheter design. For an easier insertion of the urinary catheter 10, or the insertion section 14, respectively, in a urethra of a patient, the tip 16 thus has a spherical cone 34. This spherical cone 34 serves to facilitate an easy insertion of the urinary catheter 10, wherein this can be designed such that it is as comfortable for the patient as possible.

Figure 3:
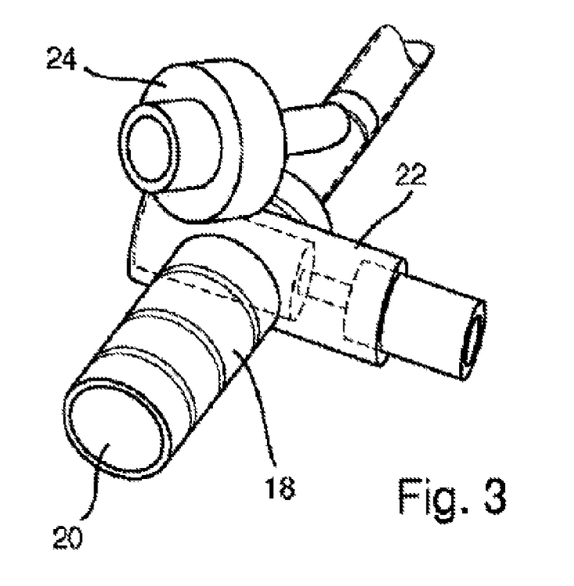
FIG. 3 shows a depiction of the connecting section of the urinary catheter.

FIG. 3 shows a detail view of the connecting section 18 of the urinary catheter 10. Connection elements such as a urine bag, for example, can be connected to the connecting section 18 through the opening 20. The alternate connecting section 24 is clearly visible in FIG. 3 and is connected to the secondary channel 30 for filling the balloon. Furthermore, the valve 22, which is designed as a slide valve, is depicted in FIG. 3 in the closed setting. The functioning of the valve 22 is described and explained in greater detail below based on FIGS. 4A and 4B.

Figure 4A:
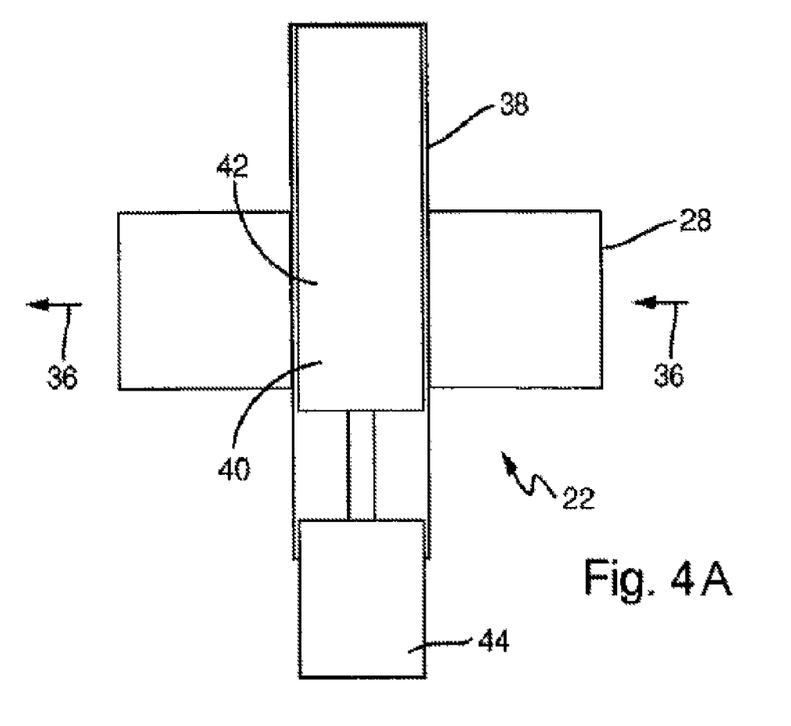
FIG. 4A shows a first embodiment of a slide valve for the urinary catheter in the closed setting.

The valve 22 is depicted in FIG. 4A in its closed setting, analogous to FIG. 3. The discharge direction of the urine through the main channel 28 is indicated by an arrow 36. An actuating element 40 for the valve 22, designed as a piston, is disposed in a receiving section 38, running transverse to the main channel 28, having a cylindrical design and intersected by the main channel 28. A closing section 42 of the actuating element 40 is located in the main channel 28, in the closed setting depicted in FIG. 4A, such that liquid can no longer be discharged through the main channel 28.

Figure 4B:
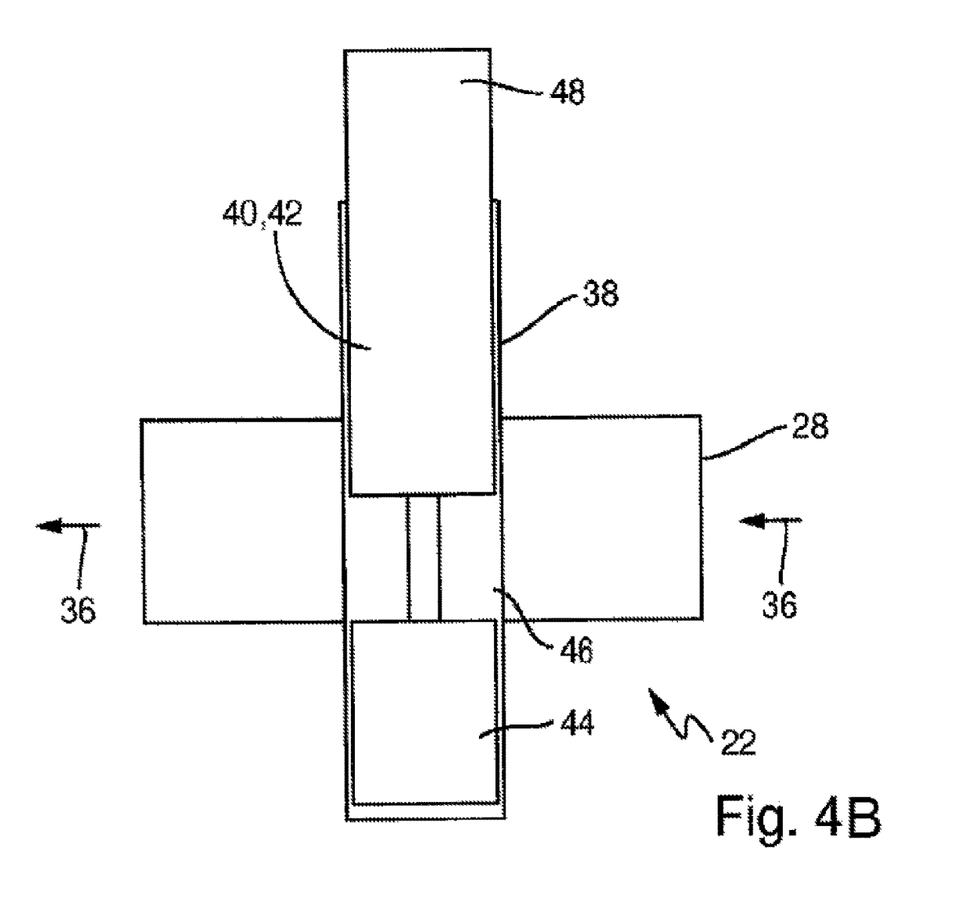
FIG. 4B shows the first embodiment of the slide valve in the releasing setting.

When pressure is applied to the lower end 44 of the actuating element 40, it is moved into the releasing setting depicted in FIG. 4B. When in this releasing setting, liquid, or urine, respectively, can flow through the main channel 28 in the direction of the arrow 36. The closing section 42 is moved thereby such that it no longer overlaps the main channel 28, in contrast to FIG. 4A. A releasing section 46 then overlaps the main channel 28. This releasing section 46 has a clearly smaller outer diameter than the receiving section 38. As a result, liquid can flow past the releasing section 46, through the main channel 28.

When a urine bag is being replaced, or after the bladder has been voided, respectively, the valve 22 for the urinary catheter can again be closed. For this, pressure should be exerted on the upper end 48 of the actuating element 40. The actuating element 40 is again moved into the closed setting in the receiving section 38. As a result, urine can no longer be discharged from the urinary catheter 10, or through the opening 20 at the connecting section 18.

Figure 5A:
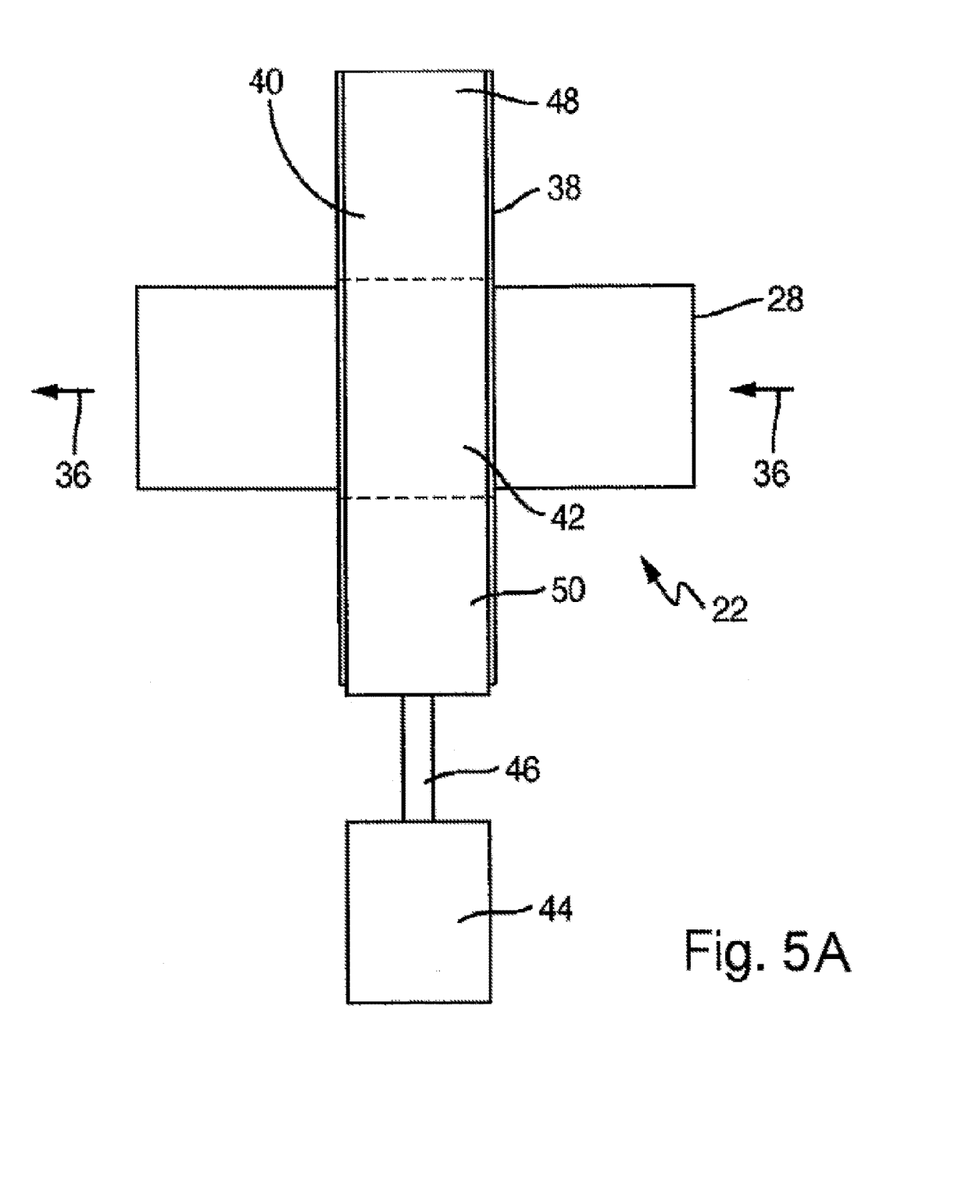
FIG. 5A shows a second embodiment of a slide valve for the urinary catheter in the closed setting.
Figure 5B:
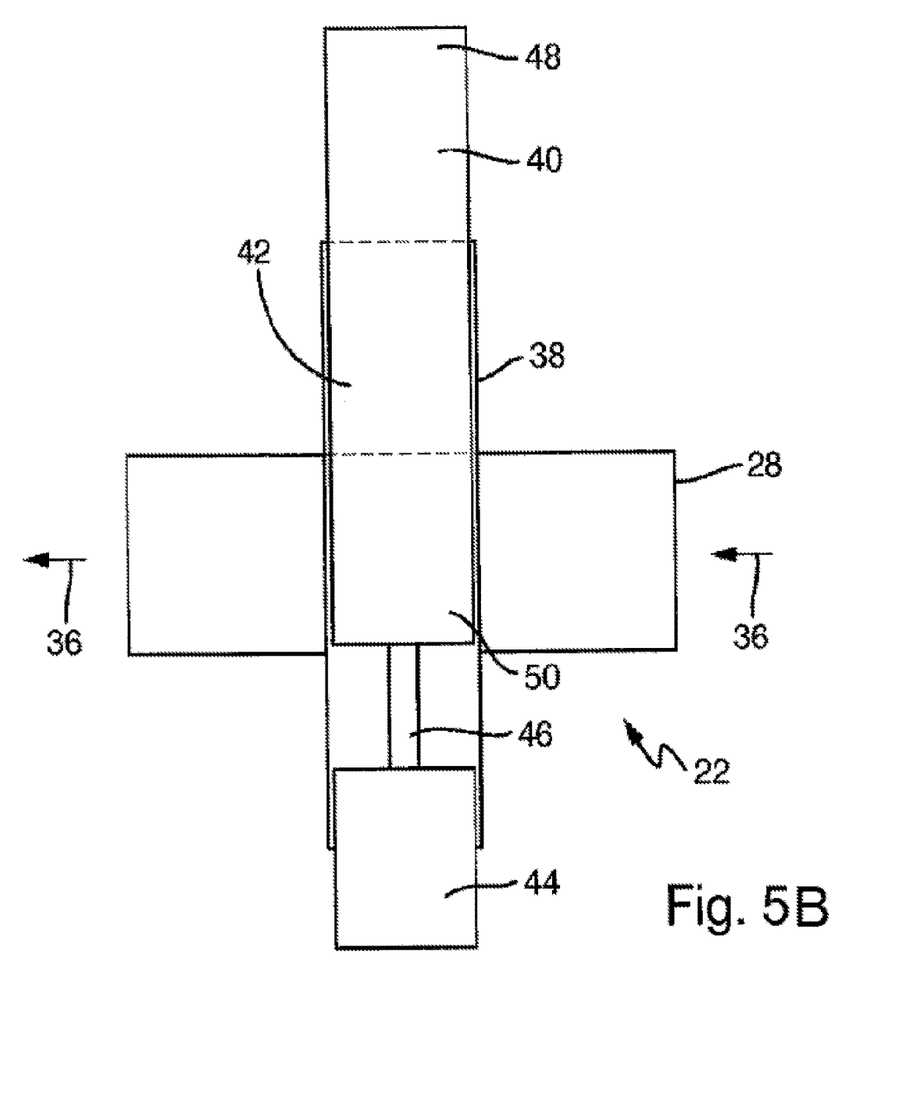
FIG. 5B shows the second embodiment of the slide valve in the middle setting.
Figure 5C:
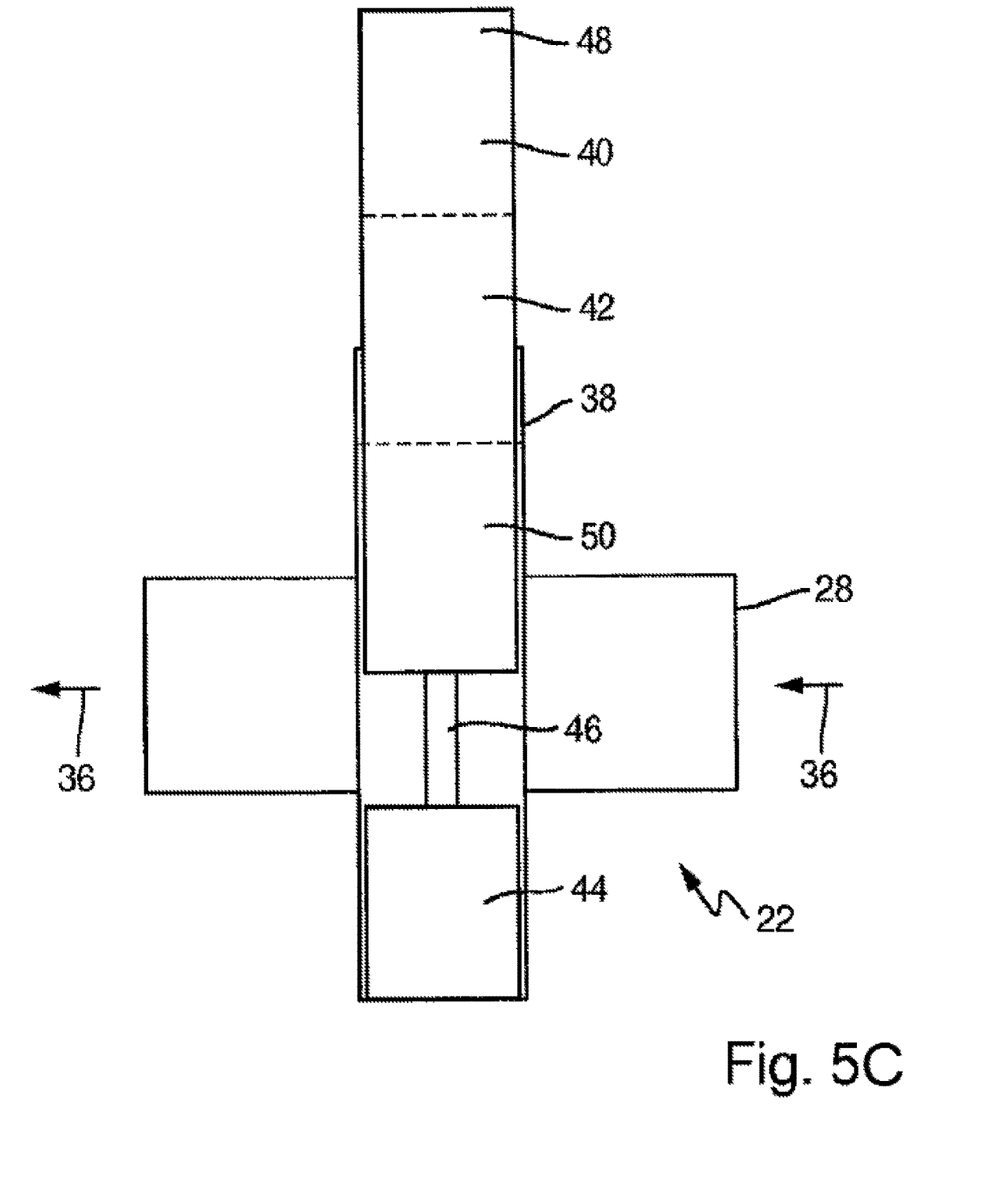
FIG. 5C shows the second embodiment of the slide valve in the releasing setting.

Another embodiment of a valve 22 for a urinary catheter 10 is shown in FIGS. 5A to 5C. The components and elements corresponding thereto in FIGS. 4A and 4B are indicated with corresponding reference symbols. The valve as shown in FIGS. 5A to 5C has three switching settings, wherein the valve 22 in FIG. 5A is depicted in a closed setting, analogous to the closed setting depicted in FIG. 3 and FIG. 4A. The discharge direction for the urine through the main channel 28 is likewise indicated by an arrow 36. An actuating element 40 for the valve 22, designed as a piston, is disposed in a receiving section 38, running transverse to the main channel 28, which is designed as a cylinder, and intersected by the main channel 28.

In the closed setting depicted in FIG. 5A, a closing section 42 of the actuating element is located in the main channel 28 such that liquid can no longer be discharged through the main channel 28. An air-permeable filter and/or membrane section 50 is disposed beneath the closing section 42. This filter and/or membrane section 50 is advantageously manufactured from a hydrophobic acrylate polymer, and cannot be permeated by liquids.

When pressure is applied to the lower end 44 of the actuating element 40, it is first moved to the middle setting depicted in FIG. 5B. The filter and/or membrane section 50 overlaps the main channel 28 when in the middle setting, such that air can be discharged through the main channel 28, but, due to the non-liquid-permeable filter and/or membrane section 50, a discharge of liquid can be prevented. As a result, air can be removed from a bladder of a patient in the middle setting.

If pressure is then applied to the lower end 44 of the actuating element 40, it is moved to the open setting depicted in FIG. 5C. Liquid, or urine, respectively, can flow in the direction of the arrow 36 through the main channel 28 when in this releasing setting. The closing section 42 is moved thereby, from the overlapping with the main channel 38, analogously to FIG. 4B. The releasing section 46 then overlaps the main channel 28. This releasing section 46 has a significantly smaller outer diameter than the receiving section 38. As a result, liquid can flow past the releasing section 46, through the main channel 28. A replacement of a urine bag can likewise occur, analogously to the valve 22 as shown in FIG. 4A and FIG. 4B, after moving the valve into the closed setting. For this, pressure should be applied to the upper end 48 of the actuating element 40, and the actuating element 40 is again moved in the receiving section 38, into the closed setting. As a result, with a valve 22 as shown FIGS. 5A to 5C as well, urine can no longer be discharged from the urinary catheter 10, or through the opening 20 at the connecting section 18, respectively.

The invention has been described in an illustrative manner. It is to be understood that the terminology which has been used is intended to be in the nature of words of description rather than of limitation. Many modifications and variations of the invention are possible in light of the above teachings. Therefore, within the scope of the appended claims, the invention may be practiced other than as specifically described.

What is claimed is:

1. A urinary catheter comprises a tube, wherein the tube has an insertion section for insertion in a bladder via a urethra, and wherein the tube has a connecting section for the connection of connection elements thereto, such that liquid can be discharged from the urethra at the connecting section wherein a closable valve is disposed between the insertion section and the connecting section such that a discharge of liquid from the connecting section can be prevented when the valve is closed, wherein the valve is designed as a slide valve, and has three switching settings, such that the valve is closed in the closed setting, the valve is air-permeable in a middle setting and the valve is open in a releasing setting, wherein the valve comprises an actuating element disposed within a receiving section of the valve running transverse to a main channel of the valve, wherein the actuating element comprises a closing section, a releasing section and a filter and/or membrane section which cannot be permeated by liquids, wherein the closing section is located in the main channel when the valve is in the closed setting, wherein the releasing section is located in the main channel when the valve is in the releasing setting and wherein the filter and/or membrane section is located in the main channel when the valve is in the middle setting.

2. The urinary catheter according to claim 1, wherein the filter and/or membrane section comprises a hydrophobic acrylate polymer.

3. The urinary catheter according to claim 1, wherein the urinary catheter has a closed hollow tip with at least two opposing openings in accordance with a Nelaton catheter design on its end facing away from the connecting section.

4. The urinary catheter according to claim 1, wherein the urinary catheter is a transurethral urinary catheter.

5. The urinary catheter according to claim 1, wherein the urinary catheter is an indwelling catheter.

6. The urinary catheter according to claim 1, wherein the urinary catheter is a flushing catheter.

* * * * *